United States Patent

Fladung

Patent Number: 5,147,304
Date of Patent: Sep. 15, 1992

[54] DEVICE SUITABLE FOR RENDERING HARMLESS THE CANNULA OF SYRINGES

[75] Inventor: Ruediger Fladung, Duderstadt, Fed. Rep. of Germany

[73] Assignee: Duderstaedter Dental-Labor GmbH, Duderstadt, Fed. Rep. of Germany

[21] Appl. No.: 690,776

[22] Filed: Apr. 26, 1991

[30] Foreign Application Priority Data

Apr. 27, 1990 [DE] Fed. Rep. of Germany ... 9004788[U]

[51] Int. Cl.$^5$ .............................................. A61M 5/00
[52] U.S. Cl. .................................................. 604/110
[58] Field of Search ................................. 604/110, 187

[56] References Cited

FOREIGN PATENT DOCUMENTS 0136392 5/1989 European Pat. Off. .
332584 9/1989 European Pat. Off. ............ 604/110
2211420 7/1989 United Kingdom .

Primary Examiner—John D. Yasko
Attorney, Agent, or Firm—Foley & Lardner

[57] ABSTRACT

In order to render harmless disposable syringe cannulae, a metal tube of a cannula is introduced into an insertion opening of a casing that comprises two electrodes that are arranged beneath the insertion opening. An electrical circuit including the metal tube of a cannula can thus be completed for the purpose of rendering the cannula unusable. The insertion opening limits insertion motion via a stop. The insertion opening has a circular shape and permits the metal tube to be inserted only in its longitudinal direction. Positioned directly beneath insertion opening are both a first electrode comprising an insertion opening capable of accommodating a metal tube and a second electrode that permits the tip of the metal tube, having penetrated through the insertion opening of first electrode, to contact the second electrode. The second electrode is provided preferably with a sloping slide face.

15 Claims, 3 Drawing Sheets

DEVICE SUITABLE FOR RENDERING HARMLESS THE CANNULA OF SYRINGES

BACKGROUND OF THE INVENTION

The present invention relates to a device which is suitable for rendering harmless the nonreusable cannulae of a syringe.

Due to the danger of infection, the majority of syringes now in use are designed for one time use only. Such syringes consist of a plastic needle body over which is slid the cannula that comprises both a metal tube and a plastic body forming the cannula head. In order to prevent the repeated use of such cannulae and the attendant spread of infection, one prior art method involves bending the cannula or its metal tube out of its normally straight shape into a bent shape in order to indicate that the cannula has already been used. After being bent out of shape, the cannulae are, more often than not, discarded in the internal garbage system. In another conventional disposal method, the still straight cannulae, after having been used once, are tossed into special containers having a pail-like jacket. After having been filled to a suitable level with used cannulae, the container is filled to the top with liquid plaster. Thus covered, the syringes are carried in the special container to the waste disposal site.

Because the method of manually bending the syringes entails both the risk of injury and contact with infected liquids, a method is disclosed in EP 0 136 392 B1 by means of which cannulae can be deformed with the aid of an electric current. Provided for this purpose is an apparatus of the type in which arranged beneath the insertion opening are two spring-mounted electrodes which, while not directly contacting each other, can be connected together via the metal tube of the cannula in a manner that permits an electrical current to flow through the metal tube of the cannula. The shape of the insertion opening permits the cannula, together with its plastic head, to be pushed inside the apparatus. A laterally-oriented longitudinal extension of the insert opening permits the head to catch when slid laterally in the direction of the longitudinal extension. A slanted guide element located on the underside of the longitudinal extension ensures the separation of the cannula from the syringe body, and allows the entire cannula together with its deformed metal tube, to fall into a drawer located inside the apparatus, the result of which being that the user has left in his hand only the syringe body, which is now open toward the bottom.

OBJECTS AND SUMMARY OF THE INVENTION

The object of the present invention is the improvement of an apparatus of the aforementioned type in respect of its handling and safety features, with a view toward reducing the chance of injury or infection.

In accordance with a first aspect of the invention, an apparatus is provided for rendering harmless the cannulae of disposable syringes, each of the cannulae having a head and a metal tube extending longitudinally from the cannula. The apparatus comprises a casing and an electrode arrangement which forms a closed electrical circuit when the metal tube is inserted into a first circular insertion opening of the casing which is capable of receiving the metal tube of a cannula only in the longitudinal direction of the metal tube. The casing also has a stop formed thereon which abuts the head of the cannula to limit insertion of the metal tube into the casing. The electrode arrangement includes a first electrode which is located directly beneath the first insertion opening and into which is formed a second insertion opening which is capable of receiving the metal tube after the metal tube is inserted through the first insertion opening. The electrode arrangement also includes a second electrode which is located directly beneath the first electrode and which is capable of contacting a tip of the metal tube after the metal tube is inserted through the second insertion opening.

In accordance with another aspect of the invention, the first electrode comprises first and second parts which have the second insertion opening formed therebetween and which are movable with respect to one another to vary the diameter of the second insertion opening. A spring is provided which biases the first and second parts towards one another.

In accordance with another aspect of the invention, a surface of the second electrode which can be contacted by the tip of the metal tube comprises a sloped side face of the second electrode.

Another object of the invention is to provide a method for rendering harmless disposable syringes provided with cannulae each having a head and a metal tube extending therefrom.

In accordance with one aspect of the invention, the method comprises the step of conducting an electric current through a metal tube of a cannula, thereby melting a portion of the metal tube via heat generated by the electric current such that the metal tube is deformed and such that a portion of the metal tube that remains on the cannula comprises a melted and closed end. In a preferred embodiment, the step of conducting an electric current comprises a first step of inserting the metal tube through an insertion opening formed in a casing of a device. A subsequent step comprises inserting the metal tube further into the casing and into a position in which the metal tube extends through a second insertion opening formed by a first electrode of an electrical circuit. A subsequent step includes inserting the metal tube further into the casing and into a position in which a tip of the metal tube contacts a second electrode of the electrical circuit, thereby completing the electrical circuit and causing the electric current to flow through the metal tube.

Other objects, features and advantages of the present invention will become apparent to those skilled in the art from the following detailed description. It should be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

The above and further objects of the invention will become more readily apparent as the invention is more clearly understood from the detailed description to follow, reference being had to the accompanying drawings in which like reference numerals represent like parts throughout, and in which.

DETAILED DESCRIPTION OF THE PREFERRED EMBODIMENTS

Figure 1:
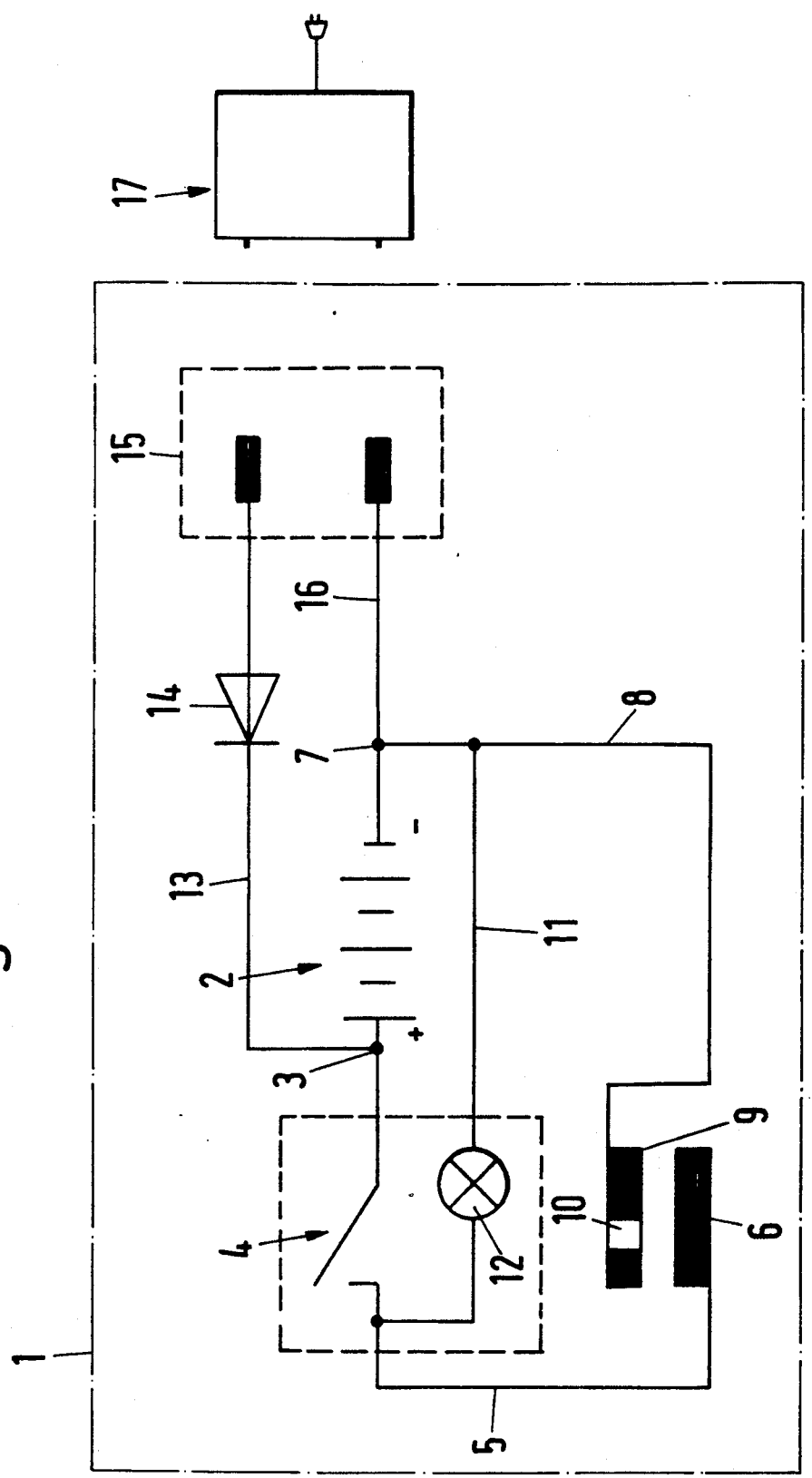
FIG. 1 is a schematic diagram of the electrical circuitry of a device constructed in accordance with a preferred embodiment of the invention.

A device suitable for rendering harmless the non-reusable cannulae of syringes comprises a casing that has an opening capable of admitting a metal tubes of the cannulae and which houses an electrode arrangement comprising two electrodes that are situated beneath the insertion opening. An electrical circuit, which includes the metal tube of the cannula, can be completed with the aid of the electrodes, for the purpose of rendering the cannula unusable.

The insertion opening limits insertion motion by means of a stop so designed as to prevent further downward movement of head of the cannula.

The objects of the invention are achieved by providing a device in which the circular shape of the insertion opening allows introduction of the metal tube only in its longitudinal direction and in which arranged directly underneath such insertion opening is a first electrode comprising a penetration opening capable of admitting the metal tube. A second electrode is arranged in such a way that the tip of the metal tube is caused to make contact with the second electrode after having been pushed through the penetration opening located in the first electrode.

In the apparatus, the cannula is introduced only in its longitudinal direction through the insertion opening of the apparatus and then thoroughly melted. What remains of the metal tube following this process comprises a blunt melted tip. Melting of the metal tube produces splinter- and tear-shaped pieces of the cannula. The first electrode, which is provided immediately beneath the 15 insertion opening, comprises an opening permitting insertion of the metal tube, and thus allows a steady electric current to flow through the metal tube which melts after impacting with its tip upon the second electrode. It is preferable, however, if the second electrode is embodied as a thick, stationary metal block that is provided at its point of contact with the metal tube tip with a slide face that slopes relative to the longitudinal direction of the metal tube. Such an arrangement improves the reliability of the apparatus.

The circular design of the insertion opening, which limits the insertion motion of the cannula preferably by means of a stop that prevents further downward movement of the cannula head, prevents the latter from being separated from the body of the syringe when inserted into the apparatus. This arrangement allows the melted cannula, including its melted and sealed end, to remain attached to the syringe body and to be discarded together with the syringe body. The cannula, which has been caused to close up by melting, forms, together with the syringe body, a closed system that prevents the escape of any infectious liquid contained therein, since withdrawal of the needle plunger in such a closed system would necessitate creation of a partial vacuum, which would, in this case, be practically impossible. Any infectious liquid trapped inside what remains of the metal tube is disinfected by the electric current passing through the metal tube. To this end, the first electrode, which is arranged directly below the insertion opening, ensures that electric current will flow through practically the entire metal tube.

In one advantageous configuration of the present invention the first electrode comprises one or more parts which the penetration opening enclose between each other. Both parts of the electrode can be moved relative to each other against the force of a spring in order to accommodate the widening of the penetration opening. When the system is not in use, the penetration opening has, advantageously, a diameter that is typical of the metal tubes normally used in conjunction with cannulae. Relative motion can be induced between the two parts of the first electrode if one part is designed to pivot relative to the other part.

In order to facilitate introduction of the cannula into the apparatus, the insertion opening is advantageously formed by a filling funnel which can, at the same time, serve as a stop for the cannula head.

The apparatus can be rendered yet more effective if the electrodes are connected to a direct current battery installed inside the casing. The battery can, in this case, be of the rechargeable type. In the present configuration, it is advantageous if, provided in the casing, is a connection site permitting a direct current battery to be recharged by means of a recharger.

A standby power switch can be arranged in the electrical circuit. It is advantageous if a light serving to indicate that the system is in a standby mode is provided in a parallel circuit. The switch, which can be operated manually, can be configured as an on/off switch. Only when the switch is closed can the system be considered ready for use and ready to process non-reusable cannulae. When the switch is opened, the electrical circuit is broken. The switch is, for this purpose, arranged in the part of the circuit that connects the anode to the direct current battery. A light serving to indicate the standby status of the system can be installed in a parallel branch of the electric circuit that bypasses the switch and the direct current battery on one side and the cathode and anode on the other. The indicator light glows when the switch is turned on.

FIG. 1 shows a casing 1 of an apparatus constructed in accordance with a preferred embodiment of the invention indicated by a broken line and also features a block diagram of the electrical circuitry for the apparatus. Housed inside the casing is a direct current battery 2, the positive pole 3 of which is connected to a switch 4. A wire 5 leads from switch 4 to an anode 6. Negative pole 7 of direct current battery 2 is connected via a wire 8 to a cathode 9 comprising two parts. An insertion opening 10 is formed between the two parts of cathode 9. A light 12 is arranged in a branch 11 that bypasses battery 2 and switch 4. It will be appreciated that the light glows only when switch 4 is closed. Direct current battery 2, which can, for example, be of the 6 volts, 6,5 Ah type, is rechargeable. A wire 13 leads from positive pole 3, via a rectifying diode 14, to a plug or box 15. A similar wire 16 leads from negative pole 7 to plug 15 to which a conventional recharging apparatus 17, which can be attached to a wall socket, can be connected.

It will be appreciated that when switch 4 is closed, the insertion of a metal tube of a cannula 28 (see FIG. 5) through insertion opening 10 in a cathode 9 will cause a circuit to be completed. Anode 6 and cathode 9 are arranged at a set distance from each other so that the desired section of metal tube 27 of cannular 28 can be melted. This process will be described in greater detail in FIG. 5.

Figure 2:
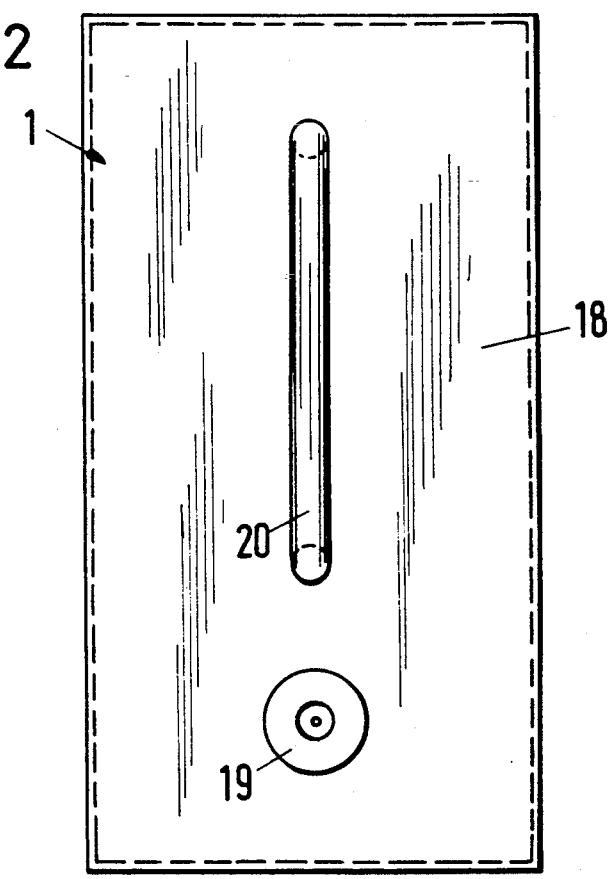
FIG. 2 is a plan view of the device of FIG. 1.
Figure 3:
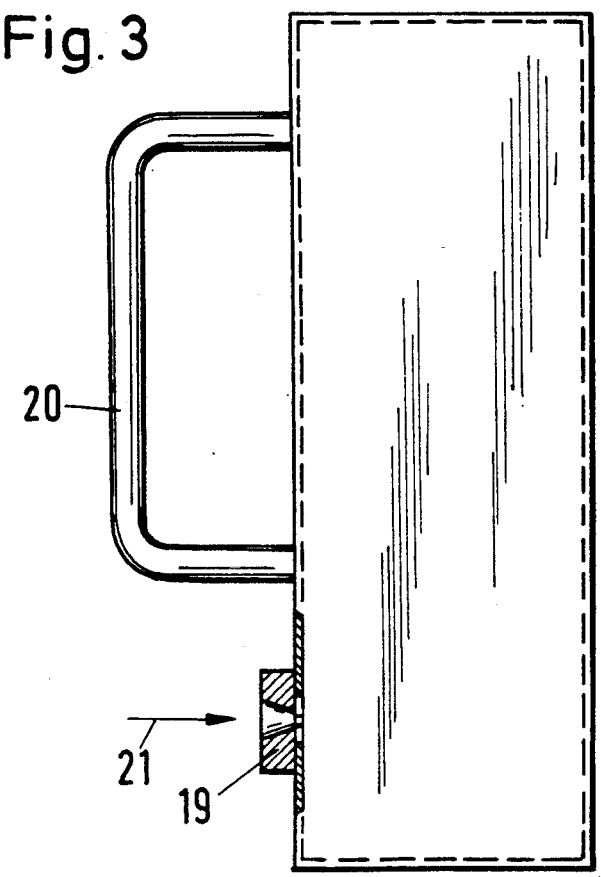
FIG. 3 is a side view of the device shown in FIG. 2.

FIG. 2 is a plan view of the apparatus together with its casing 1 which is advantageously designed to comprise a plurality of parts. Casing 1 comprises a casing cover 18 that closes the casing from the top and comprises an insertion funnel 19 on one side and a handle 20 on the other. The shape and arrangement of insertion funnel 19 predetermines that of insertion device 21 which, in the configuration of the preferred embodiment, is oriented vertically from the top to the bottom, for example, when the device sits upon a table.

Figure 4:
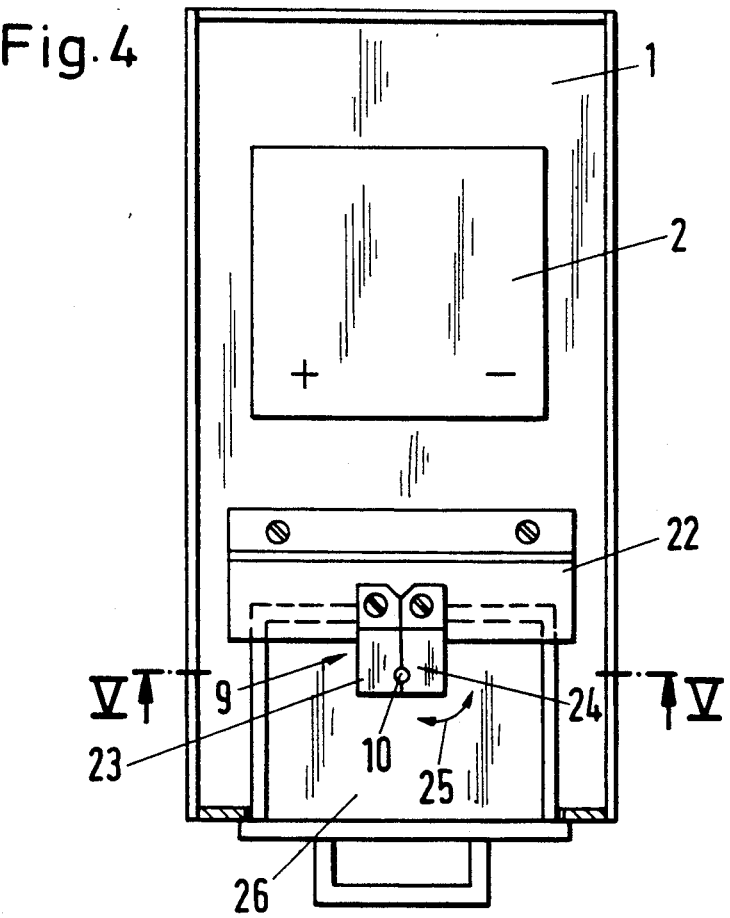
FIG. 4 is a plan view of the device of FIG. 1 with its casing cover removed.
Figure 5:
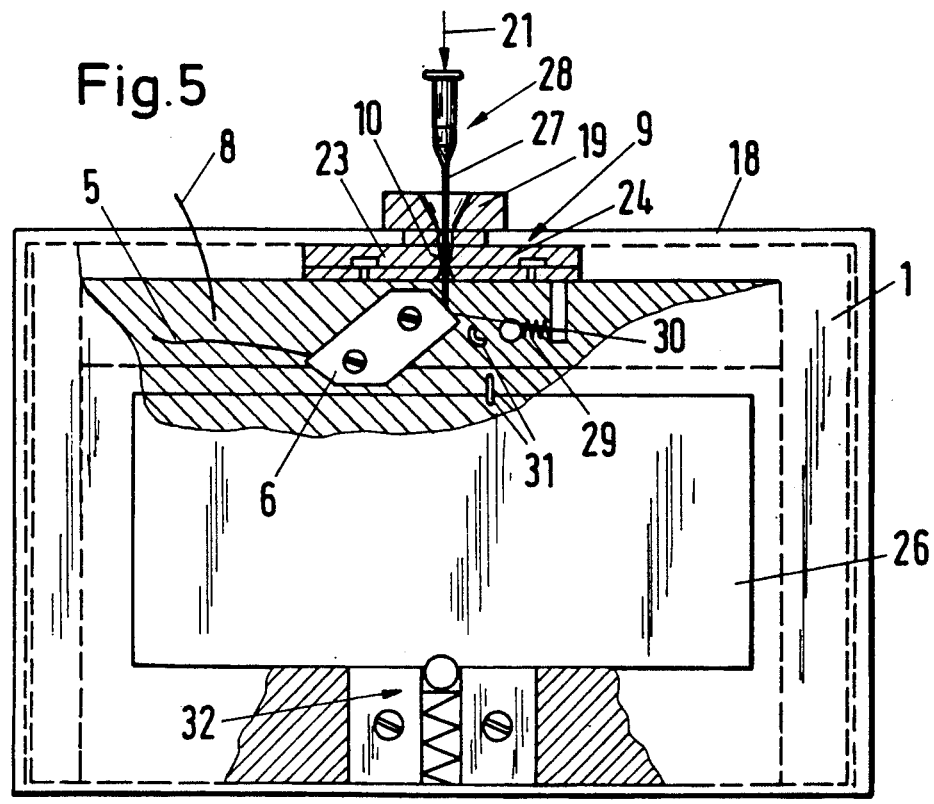
FIG. 5 is an enlarged sectional view along line V—V of FIG. 4.

FIG. 4 shows a plan view of the inside of the apparatus wherein casing cover 18 has been removed. Attention is drawn to the arrangement of direct current battery 2. Shown attached to a metal block 22, which can be attached to casing 1, are flat strips forming a stationary part 23 and a part 24 of cathode 9. Part 24 is capable of pivoting as indicated by arrow 25, in order to create insertion opening 10 between parts 23 and 24. For the purpose of clarity, anode 6 has not been included in FIG. 4. Provided beneath the unit comprising cathode 9 and anode 6 is a drawer 26 which can be pulled out of casing 1 and which serves to catch the fallen, melted cannula pieces. FIG. 5 illustrates the method of operation of the proposed apparatus. Insertion funnel 19 is screwed by means of a thread into casing cover 18 of the apparatus casing. The smallest diameter of the funnel-shaped insertion funnel still exceeds the outside diameter of metal tube 27 of cannula 28. The arrangement of insertion funnel 19 predetermines the shape of insertion device 21, which permits cannula 28 to be pushed up to its head through insertion funnel 19 and the casing to the inside of the apparatus. FIG. 5 shows both parts 23 and 24 of cathode 9 together with insertion gap 10, which is smaller than the outer diameter of metal tube 27 of cannula 28. The ability of part 24 of cathode 9 to pivot, as indicated by arrow 25 (FIG. 4), against the force of a spring 29, permits the size of insertion opening 10 to change in order to accommodate metal tube 27 of cannula 28.

When switch 4 has been closed and a syringe 28 inserted in the manner described through insertion device 21 into the device, the tip of metal tube 27 contacts directly anode 6, which, being embodied and arranged inside casing 1 as a thick isolated block of rigid metal, is connected via wire 5 to direct current battery 2. Anode 6 is arranged to slope relative to insertion device 21, or can alternatively comprise a substantially linear sloping slide face 30 of the thick metal block. This slide face facilitates completion of a circuit between cathode 9 and anode 6 whenever metal tube 27 forming part of the circuit is traversed by a current of approximately 1200 amps which induces in the metal tube a temperature high enough to readily melt the thin-walled metal tube. Produced from the melting of the metal tube are soft pieces of melted cannula 31 that fall into a drawer 26 that is arranged beneath the apparatus used for melting the metal tubes. A ball lock 32, which retains drawer 26 in its inserted position, also permits drawer 26 to be emptied. It will be appreciated that when cannula 28 is pushed in the direction of insertion opening 20, the continuous melting of syringe parts 31 cause the continuous destruction and break up of metal tube 27 of cannula 28, until the insertion phase is brought to a stop when the plastic head of the cannula meets insertion funnel 19. It is proposed that the size of the apparatus be such that even the end of the leftover, melted portion of metal tube 27 can be subjected to a heat sufficiently intense to be able to eliminate any danger of infection.

What is claimed is:

1. An apparatus for rendering harmless the cannulae of disposable syringes, each of said cannulae having a head and a metal tube extending longitudinally from said cannula, said apparatus comprising:
   (A) a casing having a first circular insertion opening formed therein which is capable of receiving the metal tube of a cannula only in the longitudinal direction of said metal tube, said casing also having a stop formed thereon which abuts the head of said cannula to limit insertion of said metal tube into said casing; and
   (B) an electrode arrangement which forms a closed electrical circuit when said metal tube is inserted into said first insertion opening, said electrode arrangement comprising
      (i) a first electrode which is located directly beneath said first insertion opening and into which is formed a second insertion opening which is capable of receiving said metal tube after said metal tube is inserted through said first insertion opening,
      (ii) a second electrode formed by a stationary, rigid metal block which has a substantially linear side face sloping to one side, said side face of said metal block being located directly beneath said first electrode and being capable of contacting a tip of said metal tube after said metal tube is inserted through said second insertion opening; and
   (C) a drawer which is located in said casing vertically beneath said first and second electrodes and which receives melted cannula pieces from said side face of said metal block.

2. An apparatus in accordance with claim 1, wherein said first electrode comprises first and second parts which have said second insertion opening formed therebetween and which are movable with respect to one another to vary the diameter of said second insertion opening, and further comprising a spring which biases said first and second parts towards one another.

3. An apparatus in accordance with claim 2, wherein the smallest possible diameter of said second insertion opening is smaller than the diameter of said metal tube.

4. An apparatus in accordance with claim 2, wherein one of said first and second parts is pivotable with respect to the other of said first and second parts.

5. An apparatus in accordance with claim 1, wherein said first insertion opening is formed by an insertion funnel.

6. An apparatus in accordance with claim 1, further comprising a direct current battery which is located within said casing and which is connectable to said first and second electrodes.

7. An apparatus in accordance with claim 6, further comprising a recharging apparatus and a connection device which is located within said casing and which connects said direct current battery to said recharging apparatus.

8. An apparatus in accordance with claim 1, wherein said stop is formed by a portion of said casing which defines said first insertion opening.

9. An apparatus for rendering harmless the cannulae of disposable syringes, each of said cannulae having an electrically conductive tube extending therefrom, said apparatus comprising:
   (A) a casing having a first insertion opening formed therein and having a stop formed thereon;

(B) an electrode arrangement which forms a closed electrical circuit when the conductive tube of a cannula is inserted into said first insertion opening, said electrode arrangement including
  (i) a first electrode which is located beneath said first insertion opening and into which is formed a second insertion opening which is capable of receiving said metal tube after said metal tube is inserted through said first insertion opening, said first electrode, including
    1) first and second parts which have said second insertion opening formed therebetween and which are movable with respect to one another to vary the diameter of said second insertion opening, and
    2) a spring which biases said first and second parts towards one another into a position in which the smallest possible diameter of said second insertion opening is smaller than the diameter of said metal tube, and
  (ii) a second electrode which is located beneath said first electrode and which is formed by a stationary, rigid metal block which has a substantially linear side face sloping to one side, said side face of said metal block being located directly beneath said first electrode and being capable of contacting a tip of said metal tube after said metal tube is inserted through said second insertion opening.

10. An apparatus in accordance with claim 9, wherein one of said first and second parts is pivotably with respect to the other of said first and second parts.

11. An apparatus in accordance with claim 9, further comprising:
  a direct currently battery which is connectable to said first and second electrodes,
  a recharging apparatus, and
  a connection device which is located within said casing and which connects said direct current battery to said recharging apparatus.

12. An apparatus in accordance with claim 9, further comprising a drawer which is located in said casing vertically beneath said first and second electrodes.

13. An apparatus in accordance with claim 9, wherein said first and second parts of said first electrode comprise flat strips.

14. A method for rendering harmless disposable syringes provided with cannulae each having a head and a metal tube extending therefrom, said method comprising the steps of:
  (A) inserting said metal tube through an insertion opening formed in a casing of a device; then
  (B) inserting said metal tube further into said casing and into a position in which said metal tube extends through a second insertion opening formed by a first electrode of an electrical circuit; and then
  (C) inserting said metal tube further into said casing and into a position in which a tip of said metal tube contacts a substantially linear sloping face of a stationary, rigid metal block forming a second electrode of said electrical circuit, thereby completing an electrical circuit and causing an electric current to flow through said metal tube which generates heat which melts a portion of said metal tube such that said metal tube is deformed, such that the melted metal flows down said side face and away from said metal tube, and such that a portion of said metal tube that remains on said cannula comprises a melted and closed end.

15. A method in accordance with claim 14, further comprising the step of inserting said metal tube further into said casing to a position in which a head of said cannula abuts a stop formed on said casing.

* * * * *